United States Patent [19]

Teraji et al.

[11] 4,338,313

[45] Jul. 6, 1982

[54] CEPHEM COMPOUNDS

[75] Inventors: Tsutomu Teraji, Osaka; Kazuo Sakane, Amagasaki; Jiro Goto, Kashikiriyama, all of Japan

[73] Assignee: Fujisawa Pharmaceutical Co., Ltd., Osaka, Japan

[21] Appl. No.: 180,295

[22] Filed: Aug. 22, 1980

Related U.S. Application Data

[63] Continuation-in-part of Ser. No. 160,904, Jun. 18, 1980, which is a continuation-in-part of Ser. No. 128,260, Mar. 7, 1980, which is a continuation-in-part of Ser. No. 116,984, Jan. 30, 1980, which is a continuation-in-part of Ser. No. 108,161, Dec. 28, 1979.

[30] Foreign Application Priority Data

Oct. 12, 1979 [GB] United Kingdom ............... 7935538

[51] Int. Cl.³ .................................... C07D 501/20
[52] U.S. Cl. ....................... 424/246; 544/25
[58] Field of Search ................ 544/25; 424/246

[56] References Cited

U.S. PATENT DOCUMENTS

| | | | |
|---|---|---|---|
| 3,821,207 | 6/1974 | Chow et al. | 544/25 |
| 4,079,178 | 3/1978 | Cook et al. | 544/25 |
| 4,093,803 | 6/1978 | Cook et al. | |
| 4,098,888 | 7/1978 | Ochiai et al. | |
| 4,166,115 | 8/1979 | Takaya et al. | 424/246 |
| 4,254,260 | 3/1981 | Takaya et al. | 544/27 |
| 4,258,041 | 3/1981 | O'Callaghan et al. | 544/25 |
| 4,263,291 | 4/1981 | Takaya et al. | 424/246 |

FOREIGN PATENT DOCUMENTS 2745246  4/1978  Fed. Rep. of Germany .

OTHER PUBLICATIONS

European Search Report EP 79 10 2224
European Search Report EP 79 10 5399

*Primary Examiner*—Nicholas S. Rizzo
*Attorney, Agent, or Firm*—Oblon, Fisher, Spivak, McClelland & Maier

[57] ABSTRACT

The present invention relates to new cephem compounds, more particularly to new 7-alkoxyimino amino-substituted thiadiazolylacetamido 3-(1-pyridiniomethyl)-3-cephem-4-carboxylate compounds, of high antimicrobial activity, and to pharmaceutically acceptable salts thereof.

8 Claims, No Drawings

CEPHEM COMPOUNDS

This application is a continuation-in-part of Parent application Ser. No. 160,904, filed June 18, 1980, which is a continuation-in-part of Parent application Ser. No. 128,260, filed Mar. 7, 1980, which is a continuation-in-part of Parent application Ser. No. 116,984, filed Jan. 30, 1980, which is a continuation-in-part of Parent application Ser. No. 108,161, filed Dec. 28, 1979.

The present invention relates to new cephem compounds and pharmaceutically acceptable salts thereof. More particularly, it relates to new cephem compounds and pharmaceutically acceptable salts thereof, which have antimicrobial activities and to process for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide process for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

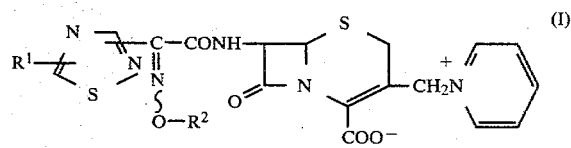

wherein
$R^1$ is amino or a protected amino group; and
$R^2$ is lower alkyl.

According to the present invention, the new cephem compounds (I) can be prepared by a process which is illustrated in the following scheme Process

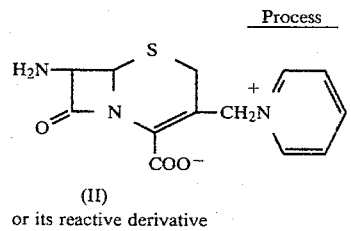

(II)
or its reactive derivative
at the amino group or a salt thereof

-continued
Process

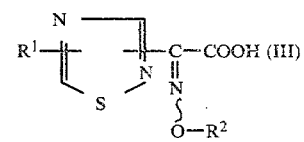

or its reactive derivative
at the carboxy group or a
salt thereof

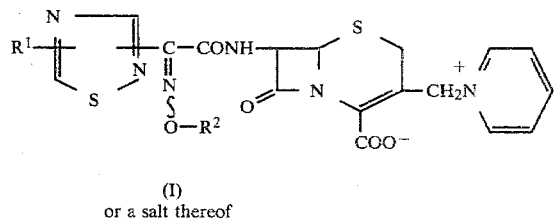

(I)
or a salt thereof wherein $R^1$ and $R^2$ are each as defined above.

Regarding the object compound (I) and the starting compound (III), it is to be understood that they include tautomeric isomers. That is, in case that the group of the formula:

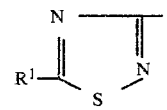

($R^1$ is as defined above) is contained in the molecules of said object and starting compounds, said group of the formula can also be alternatively represented by its tautomeric formula:

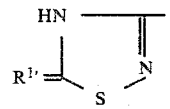

($R^{1'}$ is imino or a protected imino group). That is, the both of said groups are in the state of equilibrium each other and such tautomerism can be represented by the following equilibrium.

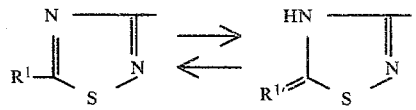

wherein $R^1$ and $R^{1'}$ are each as defined above.

These types of tautomerism between the amino-compound and the corresponding imino-compound as stated above have been well known in the literature, and it is obvious to a person skilled in the arts that both of the tautomeric isomers are easily convertible reciprocally and are included within the same category of the compound per se. Accordingly, the both of the tautomeric forms of the object compound (I) and the starting compound (III) are clearly included within the scope of the present invention. In the present specification and claims, the object and starting compounds including the group of such tautomeric isomers are represented by using one of the expressions therefor, that is the formula:

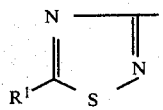

Furthermore, regarding the object compound (I) and the starting compound (III), it is to be understood that said object and starting compounds include syn isomer, anti isomer and a mixture thereof. For example, with regard to the object compound (I), syn isomer means one geometrical isomer having the partial structure represented by the following formula:

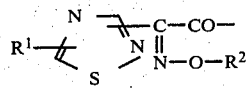

(wherein $R^1$ and $R^2$ are each as defined above) and anti isomer means the other geometrical isomer having the partial structure represented by the following formula:

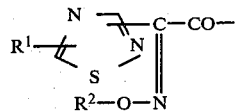

(wherein $R^1$ and $R^2$ are each as defined above).

Regarding the starting compound (III) as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected amino" for $R^1$ may include an acylamino or an amino group substituted by a conventional protecting group such as ar(lower)alkyl which may have at least one suitable substituent(s), (e.g. benzyl, trityl, etc.) or the like.

Suitable acyl moiety in the term "acylamino" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine) or the like.

Suitable "lower alkyl" for $R^2$ is one having 1 to 6 carbon atom(s) and may include methyl, ethyl, propyl, isopropyl, butyl, isobutyl, tert-butyl, pentyl, tert-pentyl, hexyl and the like, and preferably one having 1 to 4 carbon atom(s).

In the present invention, preferable example of $R^1$ is amino and preferable example of $R^2$ is lower alkyl.

The process for preparing the object compounds of the present invention is explained in details in the following.

PROCESS

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorus acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl[$(CH_3)_2N^+=CH-$]ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methyl imidazole); pentamethyleneketene-N-cyclohexylimine; diphenylketene-N-cyclohexylimine; ethoxyacetylene; 1-alkoxy-2-chloroethylene; trialkyl phosphite; ethyl polyphosphate; isopropyl polyphosphate; phosphorus pentachloride; phosphorus oxychloride; phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

In the present reaction, a syn isomer of the object compound (I) can be obtained preferably by reacting the compound (II) with the corresponding syn isomer of the starting compound (III).

In the aforementioned reaction and/or the post-treating of the reaction of the present invention, the aforementioned geometrical isomer and/or tautomeric isomer may occasionally be transformed into the other geometrical isomer and/or tautomeric isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now in order to show the utility of the object compounds (I), test data on anti-microbial activity of a representative compound of the present invention are shown below.

TEST METHOD

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

TEST COMPOUND (1) 7-[2-Ethoxyimino-2-(5-amino-1,2,4-thiadiazol-3-yl)acetamido]-3-(1-pyridiniomethyl)-3-cephem-4-carboxylate (syn isomer)

(2) 7-[2-Propoxyimino-2-(5-amino-1,2,4-thiadiazol-3-yl)acetamido]-3-(1-pyridiniomethyl)-3-cephem-4-carboxylate (syn isomer)

| Test Results | | |
|---|---|---|
| | Test Compound | |
| | (1) | (2) |
| Test Bacteria | MIC (μg/ml) | |
| B. subtilis ATCC 6633 | 0.78 | 0.39 |
| Ps. aeruginosa 2 | 3.13 | 12.50 |
| S. marcescens 35 | 1.56 | 3.13 |

The following examples are given for the purpose of illustrating the present invention.

EXAMPLE 1

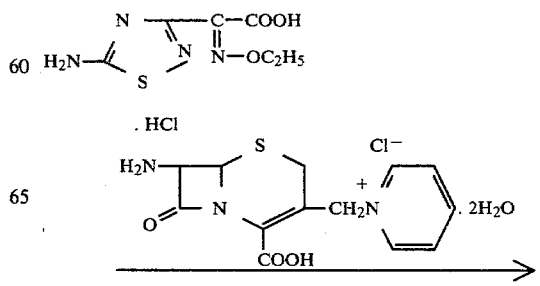

-continued

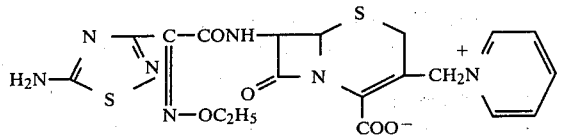

To a cold solution of phosphorus pentachloride (2.64 g) in methylene chloride (25 ml) was added 2-ethoxyimino-2-(5-amino-1,2,4-thiadiazol-3-yl)acetic acid (syn isomer) (2.48 g) at −20° C. and the mixture was stirred for 35 minutes at −20° to −14° C. To the mixture was added cold diisopropyl ether (75 ml) below −10° C. under stirring, which was continued until the mixture was warmed to ambient temperature. The resulting precipitates were collected by filtration, washed with diisopropyl ether and then kept in a desiccator for several minutes. On the other hand, a mixture of 1-[(7-amino-4-carboxy-3-cephem-3-yl)methyl]pyridinium chloride hydrochloride dihydrate (3.27 g) and trimethylsilylacetamide (16 g) in methylene chloride (50 ml) was warmed at 35° C. to make a solution, which was cooled to −20° C. To the cold solution were added the precipitates prepared above and the mixture was stirred for 25 minutes at −18° to −12° C. and for an additional 20 minutes at −12° to −3° C. A solution of sodium bicarbonate (4 g) in water (30 ml) was added to the reaction mixture and the aqueous layer was separated out, adjusted to pH 1 with 6 N hydrochloric acid, washed with ethyl acetate and then readjusted to pH 4 with an aqueous solution of sodium bicarbonate. The aqueous solution was passed through a column packed with alumina (16 g) and then subjected to column chromatography on a non-ionic adsorption resin Diaion HP-20 (trademark: prepared by Mitsubishi Chemical Industries) (100 ml). After the column was washed with water, the elution was carried out with 20% aqueous methanol. The eluates containing an object compound were collected, evaporated to remove methanol under reduced pressure and lyophilized to give white powder of 7-[2-ethoxyimino-2-(5-amino-1,2,4-thiadiazol-3-yl)acetamido]-3-(1-pyridiniomethyl)-3-cephem-4-carboxylate (syn isomer) (2.39 g), mp. 155° to 165° C. (dec.).

IR (Nujol): 3400–3150, 1770, 1660, 1610, 1530 cm$^{-1}$.

NMR (DMSO-d$_6$, δ): 1.21 (3H, t, J=7 Hz), 2.9–3.7 (2H, m), 4.12 (2H, q, J=7 Hz), 5.05 (1H, d, J=5 Hz), 5.19, 5.68 (2H, ABq, J=14 Hz), 5.7 (1H, m), 8.1 (4H, m), 8.6 (1H, m), 9.4 (3H, m).

EXAMPLE 2

The following compounds were obtained according to a similar manner to that of Example 1.

(1) 7-[2-Propoxyimino-2-(5-amino-1,2,4-thiadiazol-3-yl)acetamido]-3-(1-pyridiniomethyl)-3-cephem-4-carboxylate (syn isomer), mp. 230° to 240° C. (dec.).

IR (Nujol): 3400–3200, 1770, 1670–1600, 1530 cm$^{-1}$.

NMR (DMSO-d$_6$, δ): 0.85 (3H, t, J=7 Hz), 1.6 (2H, m), 3.06, 3.55 (2H, ABq, J=18 Hz), 4.04 (2H, t, J=6 Hz), 5.06 (1H, d, J=5 Hz), 5.18, 5.70 (2H, ABq, J=14 Hz), 5.74 (1H, dd, J=5 and 8 Hz), 8.2 (4H, m), 8.6 (1H, m), 9.5 (3H, m)

(2) 7-[2-Methoxyimino-2-(5-amino-1,2,4-thiadiazol-3-yl)acetamido]-3-(1-pyridiniomethyl)-3-cephem-4-carboxylate (syn isomer), mp. 250° to 260° C. (dec.).

IR (Nujol): 3400–3100, 1770, 1650, 1610, 1520 cm$^{-1}$.

NMR (DMSO-d$_6$, δ): 3.07, 3.57 (2H, ABq, J=18 Hz), 3.86 (3H, s), 5.06 (1H, d, J=5 Hz), 5.19, 5.69 (2H, ABq, J=14 Hz), 5.73 (1H, dd, J=5, 8 Hz), 8.0–8.3 (4H, m), 8.4–8.7 (1H, m), 9.3–9.6 (3H, m).

(3) 7-[2-Isopropoxyimino-2-(5-amino-1,2,4-thiadiazol-3-yl)acetamido]-3-(1-pyridiniomethyl)-3-cephem-4-carboxylate (syn isomer), mp. 160° to 165° C. (dec.).

IR (Nujol): 3270, 3180, 1770, 1660, 1610, 1525 cm$^{-1}$.

NMR (DMSO-d$_6$+D$_2$O, δ): 1.22 (6H, d, J=6 Hz), 3.15, 3.57 (2H, ABq, J=18 Hz), 4.17–4.60 (1H, m), 5.12 (1H, d, J=5 Hz), 5.33, 5.70 (2H, ABq, J=14 Hz), 5.78 (1H, d, J=5 Hz), 8.0–8.4 (2H, m), 8.47–8.83 (1H, m), 9.33–9.67 (2H, m).

What we claim is:

1. Cephem compounds comprising the syn isomer of the formula:

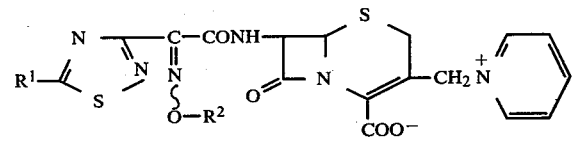

wherein
R$^1$ is amino or a protected amino group, and
R$^2$ is lower alkyl of from 1 to 6 carbon atoms, and pharmaceutically acceptable salts thereof.

2. A compund of claim 1, wherein R$^1$ is amino.

3. A compound of claim 2, wherein R$^2$ is methyl, ethyl, propyl or isopropyl.

4. The compound 7-[2-methoxyimino-2-(5-amino-1,2,4-thiadiazol-3-yl)acetamido]-3-(1-pyridiniomethyl)-3-cephem-4-carboxylate (syn isomer).

5. The compound 7-[2-ethoxyimino-2-(5-amino-1,2,4-thiadiazol-3-yl)acetamido]-3-(1-pyridiniomethyl)-3-cephem-4-carboxylate (syn isomer).

6. The compound 7-[2-propoxyimino-2-(5-amino-1,2,4-thiadiazol-3-yl)acetamido]-3-(1-pyridiniomethyl)-3-cephem-4-carboxylate (syn isomer).

7. The compound of 7-[2-isopropoxyimino-2-(5-amino-1,2,4-thiadiazol-3-yl)acetamido]-3-(1-pyridiniomethyl)-3-cephem-4-carboxylate (syn isomer).

8. An antibacterial composition comprising an effective amount of a compound of claim 1 in association with a pharmaceutically acceptable, substantially nontoxic carrier or excipient.

* * * * *